United States Patent [19]
Taepke

[11] Patent Number: 5,354,318
[45] Date of Patent: Oct. 11, 1994

[54] METHOD AND APPARATUS FOR MONITORING BRAIN HEMODYNAMICS

[75] Inventor: Robert T. Taepke, Coon Rapids, Minn.

[73] Assignee: Medtronic, Inc., Minneapolis, Minn.

[21] Appl. No.: 56,695

[22] Filed: Apr. 30, 1993

[51] Int. Cl.$^5$ .......................................... A61N 1/365
[52] U.S. Cl. .......................................... 607/22; 607/23; 607/125; 128/637; 128/661.08; 128/673; 128/692
[58] Field of Search ..................... 607/21–24, 607/14, 119, 122, 123, 125; 128/642, 637, 673, 675, 691, 692, 662.06, 662.03, 661.07–661.09, 634

[56] References Cited

U.S. PATENT DOCUMENTS

| | | |
|---|---|---|
| 4,332,259 | 6/1982 | McCorkle, Jr. ..................... 607/123 |
| 4,589,419 | 5/1986 | Laughlin . |
| 4,598,716 | 7/1986 | Hileman . |
| 4,750,495 | 6/1988 | Moore . |
| 4,856,529 | 8/1989 | Segal ............................... 128/673 X |
| 4,867,160 | 9/1989 | Schaldach . |
| 4,899,751 | 2/1990 | Cohen . |
| 4,947,852 | 8/1990 | Nassi et al. ..................... 128/662.06 |
| 4,967,748 | 11/1990 | Cohen . |
| 4,967,749 | 11/1990 | Cohen . |
| 5,156,154 | 10/1992 | Valenta et al. .................. 128/661.09 |

FOREIGN PATENT DOCUMENTS

| | | | |
|---|---|---|---|
| 0301323 | 2/1989 | European Pat. Off. ............ | 607/122 |
| 1690787 | 11/1991 | U.S.S.R. ............................. | 607/122 |

OTHER PUBLICATIONS

"Perivascular Impedance Sensors for In Vivo Chronic Blood Measurement: Detection Systems for Automatic Defibrillators, Cardioverters and Blood Pressure Controllers" by Tacker et al., 37th ACEMB, Sep., 1984 p. 20.

"A New Implantable Arterial Blood Sensor for Detection of Ventricular Fibrillation" by Konrad et al. published in Medical Instrumentation, Dec., 1988 vol. 22(6):304–311.

Primary Examiner—Lee S. Cohen
Assistant Examiner—Jeffrey R. Jastrzab
Attorney, Agent, or Firm—Reed A. Duthler; Harold R. Patton

[57] ABSTRACT

A sensor lead for use in conjunction with an implantable monitoring or therapeutic device. The lead is provided with a V-shaped bend near its distal end, and carries a blood parameter sensor distal to the V-shaped bend. The blood parameter sensor may be, for example, an oxygen sensor, a pulse sensor or a flow sensor. The V-shaped bend facilitates the location of the sensor in an internal jugular vein, allowing the sensor to be used to monitor blood flow from the brain.

10 Claims, 5 Drawing Sheets

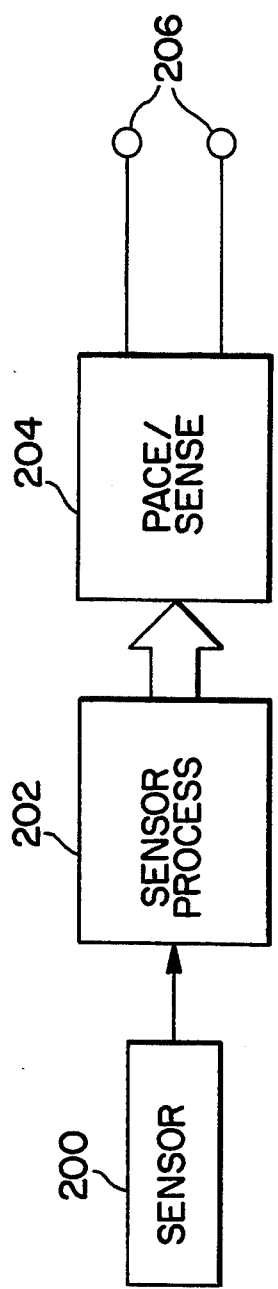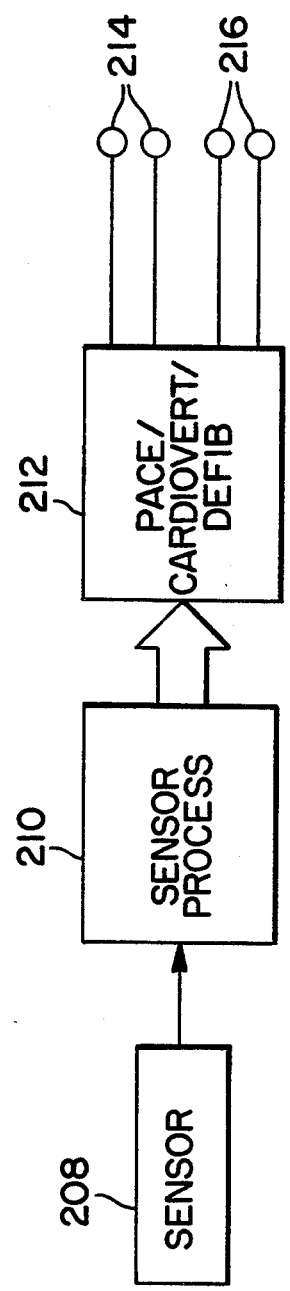

METHOD AND APPARATUS FOR MONITORING BRAIN HEMODYNAMICS

BACKGROUND OF THE INVENTION

This invention relates generally to sensors for measurement of blood flow parameters and more specifically to the use of such sensors in conjunction with implantable medical devices.

In a number of medical and surgical procedures, it is desirable to monitor blood parameters, in the course of diagnostic testing or monitoring of cardiovascular system performance. Blood parameters may also be employed to control the operation of an implantable device. For example, it is known that a relationship exists between central venous blood pressure and heart rate and that blood pressure may be employed to regulate pacing rate. Similarly, central venous oxygen saturation, Ph, temperature and other blood parameters have all been employed to regulate pacing rate.

It is also known that high rate ventricular tachycardias and ventricular fibrillation have marked effects on hemodynamic performance and that the compromise in hemodynamic performance may be measured in either the arterial or venous system. Blood parameters are recognized as being useful in this context to assist in diagnosing and monitoring of tachyarrhythmias and in controlling the operation of anti-tachycardia devices.

The direct measurement of arterial blood flow parameters using sensors introduced into the left heart or the arterial system has been proposed, but is not presently practiced in the context of chronically implantable monitoring or therapeutic devices. The primary concern with chronic implant of a sensor in the arterial system is that the introduced sensor may provoke thrombus formation and/or embolization due to the difficulty of providing a high pressure seal at the point of entry to the heart chamber or artery. Moreover, chronic implantation often results in the accumulation of fibrotic material on the implanted device, raising the possibility of obstruction of the artery. In order to avoid these problems, the use of a perivascular transducer placed adjacent to or around the exterior vascular wall of the selected artery has been proposed. However, such a device may itself poses the risk of erosion and rupture of the artery or constriction of the artery either directly or by tissue growth around the transducer. Thus, most proposals or using chronically implanted sensors have focused on sensors located in the venous system.

U.S. Pat. Nos. 4,899,751 and 4,967,749 issued to Cohen disclose pressure sensors located in a variety of locations within the venous and arterial systems. The Cohen patents disclose the use of measured blood pressure to control implantable devices such as cardiac pacemakers or anti-tachycardia devices. Similarly, U.S. Pat. No. 4,967,748, issued to Cohen discloses the use of oxygen saturation sensors, located in the vascular system for controlling operation of implantable antitachycardia devices. U.S. Pat. No. 4,750,495 discloses the use of oxygen saturation sensors for controlling operation of implantable pacemakers.

The article "Perivascular Impedance Sensors for In Vivo Chronic Blood Measurement: Detection Systems for Automatic Defibrillators, Cardioverters and Blood Pressure Controllers" by Tacker et al., published in the proceedings of the 37th ACEMB, September, 1984, page 20 and the article "A New Implantable Arterial Blood Sensor for Detection of Ventricular Fibrillation" by Konrad et al, published in *Medical Instrumentation*, December, 1988, Vol. 22(6): 304–311 both disclose sensors for measurement of arterial blood flow to the brain. The Tacker and Konrad articles suggest that placing the transducer within the arterial system as suggested in the Cohen patent is disadvantageous, and therefore disclose sensors located adjacent to but outside of the carotid or femoral arteries.

The Cohen and Moore et al patents and the Konrad and Tacker articles are indicative of the types of devices with which sensors made and used according to the present invention may usefully be employed, and are all incorporated herein by reference in their entireties.

SUMMARY OF THE INVENTION

The present invention provides a blood parameter sensor mounted on a permanently implantable lead. The sensor is intended to sense parameters associated with flow of blood to the brain. However, rather than inserting the lead into the carotid artery, the lead is inserted into the internal jugular vein.

In its most general sense, the sensor may be any sensor adapted to measure a blood parameter, including but not limited to flow sensors, pressure sensors, oxygen saturation sensors, and the like. In one disclosed embodiment the sensor takes the form of a pulse Doppler flow sensor and is employed to measure blood flow to the brain. The sensor is adapted to measure flow in the internal jugular vein, rather than in the carotid artery. As such, the pulsatile characteristics of the measured flow will be substantially reduced as compared to the flow through the carotid artery. However, the average measured flow will be comparable. This approach to measuring blood flow to the brain avoids the difficulties attendant to placement of a sensor in or around the carotid artery.

The sensor is mounted on a transvenous lead extending from an implanted stimulator or monitoring device. The lead is configured to display a resilient V-shaped bend a few centimeters from its distal end, and the sensor is mounted distal to the bend. The bend may be produced by molding the lead to display the bend, by employing an internal wire or coil to cause the lead body to display the bend, or both. The lead may be introduced through the subclavian vein, with the distal end folded back against the remainder of the lead body. The folded lead is advanced until the distal end of the lead passes the entrance to the interior jugular vein. The lead is then withdrawn slightly to allow the distal end to enter the interior jugular vein. The lead is then further withdrawn until the V-shaped bend is located at the junction of the subclavian and interior jugular veins. The V-shaped bend serves to stabilize the lead in this location, with the sensor located within the interior jugular vein.

The lead is thereafter connected to an implantable monitoring device or to an implantable therapeutic device, such as a drug dispenser or cardiac stimulator. The sensor output may simply be stored by the device or it may be employed to assist in diagnosis of arrhythmias. If the device is a cardiac stimulator, the sensor output may be employed to regulate stimulation parameters or to select between various treatment options, such as antitachycardia pacing, cardioversion or fibrillation. If the device is a drug dispenser, the sensor output may be employed to regulate the drug delivery regimen or to trigger delivery of a desired drug such as an anti-arrhythmic drug.

BRIEF DESCRIPTION OF THE DRAWINGS

FIG. 6 is a block functional diagram of an implantable rate-responsive pacemaker employing the present invention.

FIG. 7 is a block functional diagram of an implantable pacemaker/cardioverter/defibrillator employing the present invention.

DETAILED DESCRIPTION OF THE PREFERRED EMBODIMENTS

Figure 1:
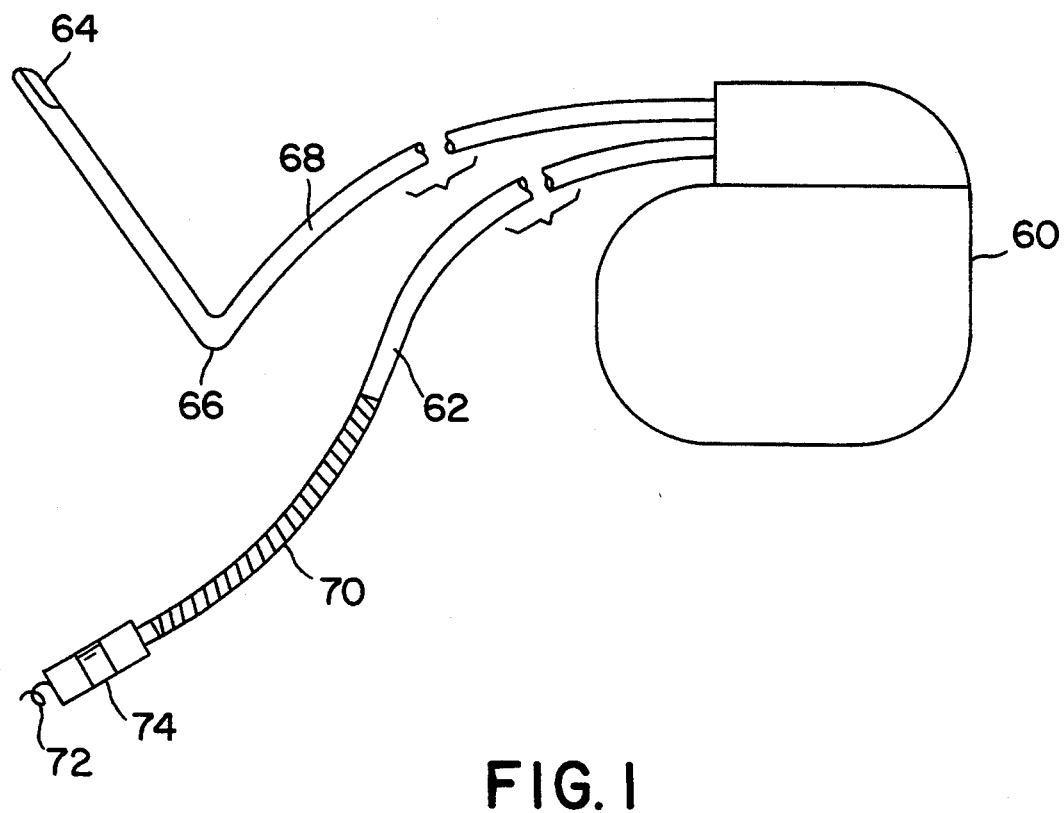
FIG. 1 is a diagram illustrating a tachyarrhythmia control device, employing the present invention.
Figure 2:
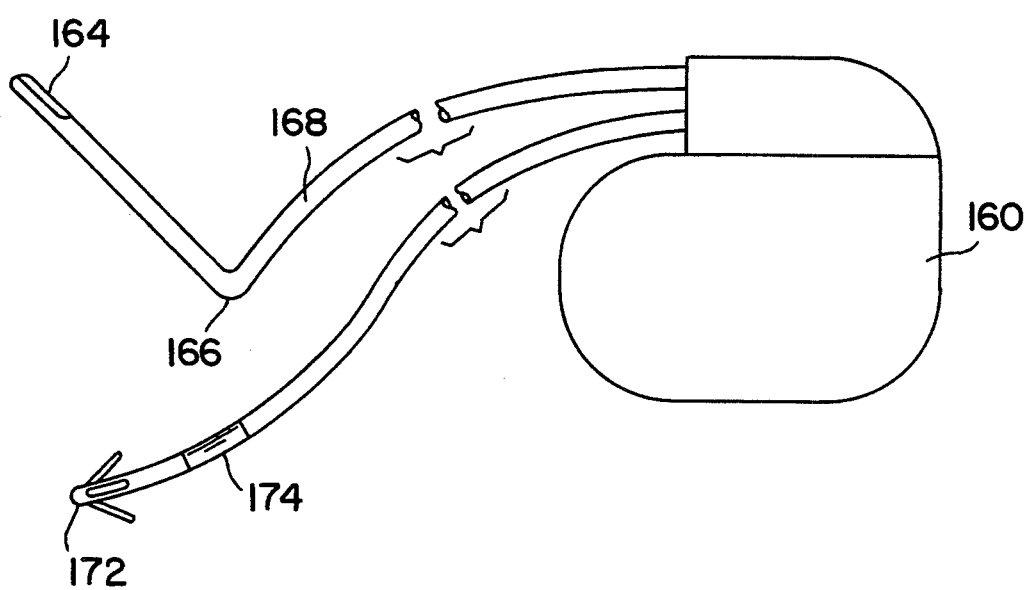
FIG. 2 is a diagram illustrating a rate responsive cardiac pacemaker, employing the present invention.

FIGS. 1 and 2 illustrate an implantable anti-tachyarrhythmia device and a cardiac pacemaker, respectively, each employing a sensor lead according to the present invention.

As illustrated in FIG. 1, a first embodiment of the present invention has three primary components including an implantable pacemaker/cardioverter/defibrillator 60; a lead 62 which carries pacing electrodes 72 and 74 and a defibrillation electrode 70; and a lead 68, carrying sensor 64 located distal to V-shaped bend 66. Bend 66 preferably defines an angle of 10 to 120 degrees, more preferably less than 90 degrees. The metal housing of pacemaker/cardioverter/defibrillator 60 serves as the second defibrillation electrode.

FIG. 2 illustrates an alternative embodiment of the present invention in which the sensor lead 168 is employed in conjunction with an implantable pacemaker 160. The lead 162 carries pacing and sensing electrodes 172, 174, for sensing ventricular depolarizations and for pacing the heart. Lead 168 corresponds to lead 68, illustrated in FIG. 1, with sensor 164 corresponding to sensor 64.

Various sensors may be employed in the context of the present invention, as discussed above. However, for purposes of the illustrated embodiments, sensors 64 and 164 may be oxygen saturation sensors, pressure sensors or piezo-electric crystals used as Doppler flow sensors. Appropriate oxygen, pressure and flow sensors are discussed below.

Figure 3:
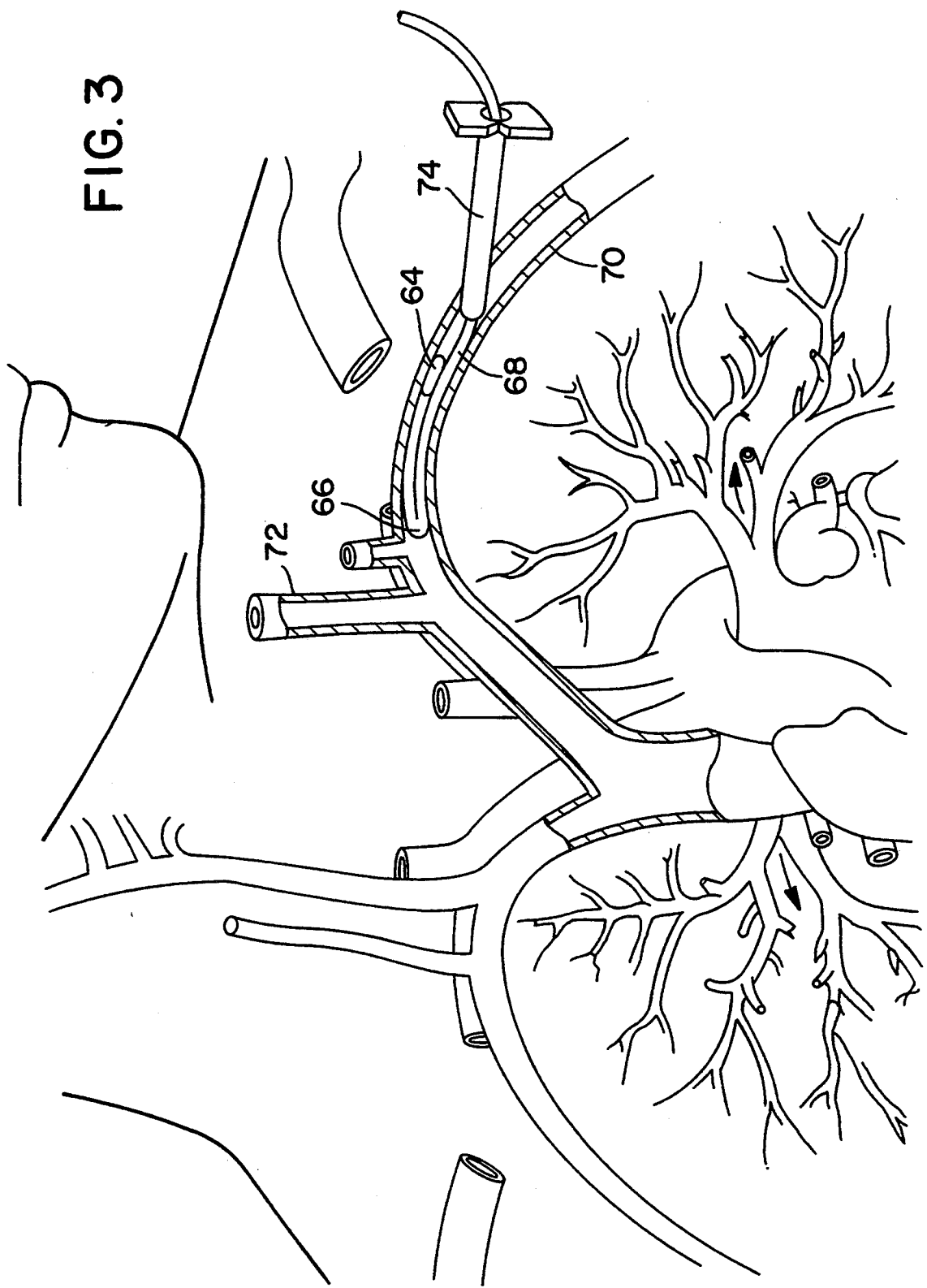
FIG. 3 illustrates insertion of the lead into the subclavian vein.

FIG. 3 is a cut away view of the left chest area, illustrating the left subclavian vein 70 and its junction with the left interior jugular vein 72, both of which are also shown in cut away form. Insertion of the lead 68 is accomplished by means of a permanent pacing lead introducer sheath 74, of conventional type. The distal end of lead 68 is folded back against itself at V-shaped bend 66 and advanced under fluoroscopic observation until its distal end has reached or passed the junction with the interior jugular vein 72. Proper positioning of the distal end of the lead for entry into the interior jugular vein 72 is verified and the lead is then withdrawn so that sensor 64 is advanced upward into the interior jugular vein 72.

Figure 4:
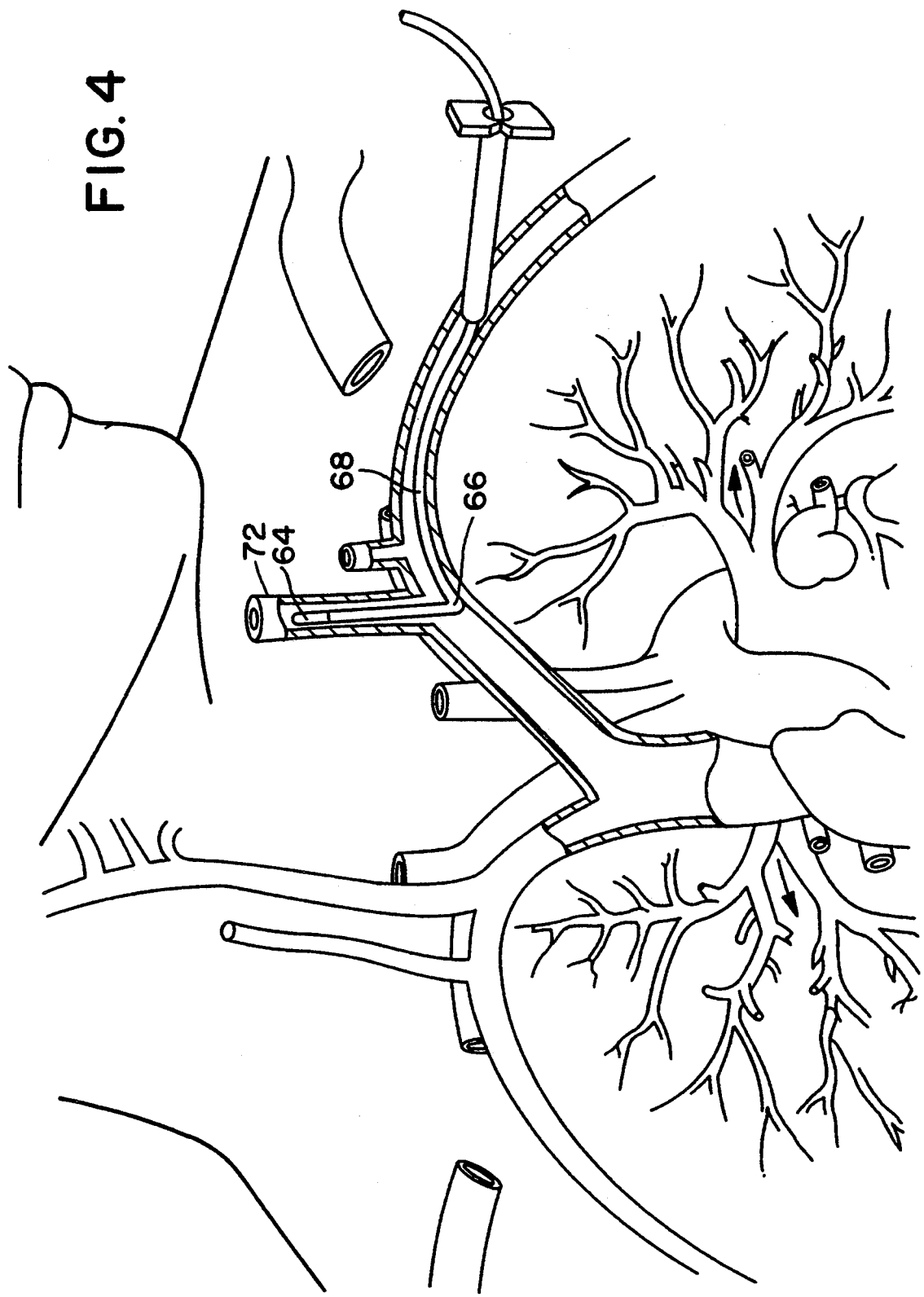
FIG. 4 illustrates the lead located with its distal end in the interior jugular vein.
Figure 5:
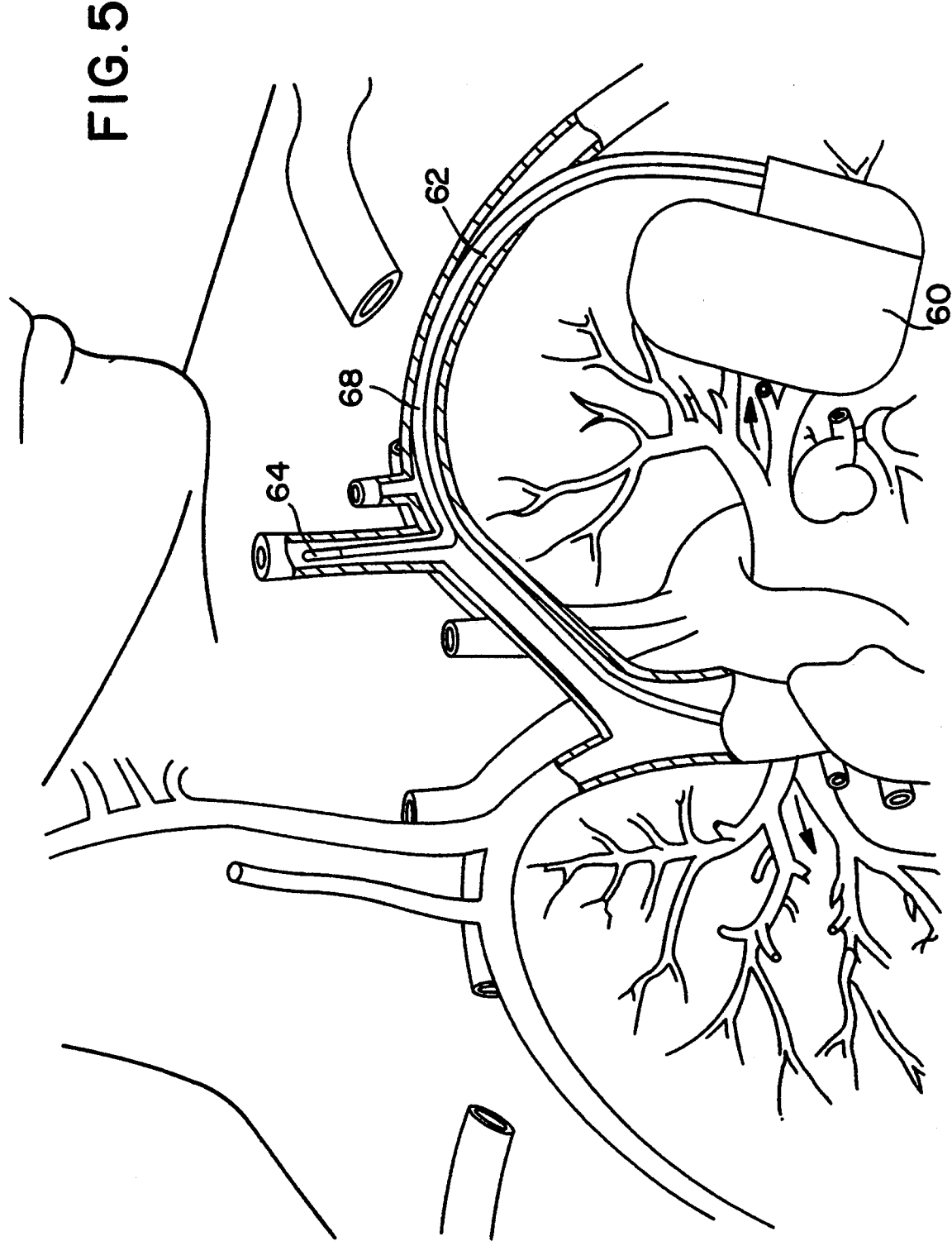
FIG. 5 illustrates the lead as implanted, coupled to an implantable pacemaker/cardioverter/defibrillator.

The final position of lead 68 is illustrated in FIG. 4. Subsequent displacement of the sensor 64 is prevented by bend 66. FIG. 5 illustrates the system of FIG. 1, as implanted. In addition to the components illustrated in FIGS. 3 and 4, Implantable pacemaker/cardioverter/defibrillator 60 (FIG. 1) is illustrated, coupled to lead 68 and to lead 62 (FIG. 1).

FIGS. 6 and 7 are block functional diagrams illustrating the integration of the sensor leads illustrated in FIGS. 1–5 into implantable pacemakers and implantable pacemaker/cardioverter/defibrillators. The various components of the block diagrams in FIGS. 6 and 7 are well known to the art and are described in detail (although not in the combined form as disclosed herein) in the prior art patents and publications cited below. The specific circuitry and structures employed to implement the functional subassemblies are thus not described in detail herein, however, their general organization and function is as follows.

FIG. 6 illustrates an implantable pacemaker in which a sensor 200, which may correspond to sensor 164, illustrated in FIG. 2, is coupled to sensor processing circuitry 202 to provide a signal for controlling the operation of pacing circuitry 204, to vary the pacing rate of pacing pulses applied to pace/sense electrodes 206. In the event that sensor 200 takes the form of a Doppler flow sensor, piezo-electric crystals may be employed as pulse Doppler transducers for monitoring blood flow, as discussed in U.S. Pat. No. 4,589,419, issued to Laughlin et al., incorporated herein by reference in its entirety. Alternatively, Doppler flow sensors as manufactured by Millar Instruments, Inc. may be employed. Sensor drive and sensor processing circuitry as described in U.S. Pat. No. 4,598,716 issued to Hileman, incorporated herein by reference, may be employed to create a signal at the output of sensor processing circuitry 202 to be applied as a control signal to pacing circuitry 204. In a fashion analogous to that disclosed for processing pressure measurements in U.S. Pat. No. 4,899,751, issued to Cohen and incorporated herein by reference in its entirety, the measured average flow velocity in the jugular vein may be compared to a long term average flow velocity. In the event that the short term average differs from the long term average by more than a predetermined value, pacing rate is increased.

In the event that the sensor 200 takes the form of a pressure sensor, the sensor processing circuitry 202 and pacing circuitry 204 may correspond to those disclosed in the above-cited U.S. Pat. No. 4,899,751, issued to Cohen. As in the Cohen patent, the short term average pressure may be measured and compared to a long term average pressure. In the event that the short term average differs from the long term average by more than a predetermined value, pacing rate is increased.

In the event that the sensor 200 takes the form of an oxygen sensor, sensor 200 and sensor processing circuitry 202 may correspond to those described in U.S. Pat. No. 4,750,495, issued to Moore et al and incorporated herein by reference in its entirety. In such an embodiment, a decrease in oxygen saturation as measured in the jugular vein would trigger an increase in pacing rate.

In the embodiments described above, stress testing of the patient may be employed by the physician to determine the relationship between sensor output and natural heart rate during conditions of normal heart function. This information may be used by the programmer associated with the pacemaker to generate a look up table for determination of appropriate pacing rates, in a fashion analogous to that disclosed in U.S. Pat. No. 4,867,160, issued to Schaldach and incorporated herein in its entirety. Alternatively, the relationship between these parameters as derived from a population of patients may be employed to generate look-up tables or mathematical relationships, stored in the pacemaker at time of manufacture, for specifying pacing rate as a function of sensor output.

FIG. 7 illustrates an implantable pacemaker/cardioverter/defibrillator employing the present invention. As discussed above, sensor 208 may take the form of a flow sensor, a pressure sensor, an oxygen saturation sensor, or other sensor of a blood parameter. Pacemaker/cardioverter/defibrillation circuitry 212 may correspond generally to circuitry disclosed in U.S. Pat. No. 4,967,749 issued to Cohen, incorporated herein by reference in its entirety. Sensor processing circuitry 210 may correspond to the circuitry discussed in conjunction with sensor processing circuitry 202 in FIG. 6. Pace/sense electrodes 214 may correspond to any prior art cardiac pacing electrodes and cardioversion/defibrillation electrodes 216 may correspond to any known cardioversion/defibrillation electrodes, as discussed in conjunction with FIG. 2, above.

In general, sensor 208 provides a signal to sensor processing circuitry 210 which varies dependant upon a parameter of the blood flowing from the brain via the jugular vein. In a fashion analogous to that disclosed in the above-cited Cohen '749 patent, measured blood parameters may be employed as an indication of unstable ventricular tachycardia, requiring delivery of a cardioversion pulse or as an indication of ventricular fibrillation, requiring delivery of a defibrillation pulse. In a device otherwise as disclosed in the cited Cohen '749 patent, short term average pressure or flow values which differ from a predetermined threshold or long term average by more than a predetermined value, in conjunction with a high heart rate, may trigger delivery of a cardioversion pulse or a defibrillation pulse.

Similarly, measured oxygen saturation may be employed to detect an unstable tachycardia or fibrillation and trigger delivery of an appropriate cardioversion or defibrillation therapy as in U.S. Pat. No. 4,967,748, issued to Cohen, also incorporated herein by reference in its entirety or as in U.S. Pat. No. 5,176,137, issued to Erickson et al and also incorporated herein in its entirety, While the above disclosures relate to the use of the sensors discussed in the context of implantable pacemakers and implantable pacemaker/cardioverter/defibrillators, it is also believed that sensors for monitoring blood parameters in the jugular vein may also be usefully employed in the context of an implantable drug dispenser. While not discussed in detail herein, it is envisioned that such sensors may be used to modulate the flow of cardiac drugs on a chronic basis or may be used to initiate the flow of cardiac drugs on an acute basis. Similarly, it is believed that sensors as disclosed in the above application may be employed to provide useful diagnostic information for storage and telemetry to an external receiver, for use by the physician in monitoring and diagnosing the patient's condition, even in the absence of apparatus for delivering electrical or drug therapies. Therefore, the above disclosure should be considered exemplary rather than limiting, rather with regard to the claims that follow.

In conjunction with the above specification, I claim:

1. A method of measuring a blood parameter in a jugular vein, comprising:

positioning a sensor which provides an output which varies as a function of said blood parameter on transvenous lead having a lead body having a "V" shaped bend near its distal end, such that said sensor is located distal to said bend;

folding said lead at said bend such that said distal end is folded back against said lead body and advancing said folded lead through a vein which intersects said jugular vein, until the distal end of said lead reaches said jugular vein;

withdrawing said lead to position said sensor in said jugular vein; and employing said sensor to measure said blood parameter.

2. A method according to claim 1 wherein said employing step comprises coupling said lead to a device comprising means for measuring the output of said sensor.

3. A method for regulating a pacing rate of a cardiac pacemaker as a function of a blood parameter, comprising:

positioning a sensor which provides an output which varies as a function of said parameter on a transvenous lead having a lead body having a "V"-shaped bend near its distal end, such that said sensor is located distal to said bend;

folding said lead at said bend such that said distal end is folded back against said lead body and advancing said folded lead through a vein which intersects a jugular vein, until the distal end of said lead reaches said jugular vein;

withdrawing said lead to position said sensor in said jugular vein;

employing said sensor within said jugular vein to measure said parameter; and varying the pacing rate of said cardiac pacemaker as a function of said measured parameter.

4. A method of controlling a therapy delivered by an implantable anti-tachycardia device as a function of a blood parameter, comprising:

positioning a sensor which provides an output which varies as a function of said parameter on a transvenous lead having a lead body having a "V" shaped bend near its distal end, such that said sensor is located distal to said bend;

folding said lead at said bend such that said distal end is folded back against said lead body and advancing said folded lead through a vein which intersects a jugular vein, until the distal end of said lead reaches said jugular vein withdrawing said lead to position said sensor in said jugular vein;

employing said sensor within said jugular vein to measure said parameter; and controlling a therapy to be delivered as a function of said measured parameter.

5. Apparatus for measuring a blood parameter, comprising:

a transvenous lead body having proximal and distal ends and having a "V" shaped bend near its distal end and having a first straight segment extending from said bend to said distal end and a second straight segment extending proximal from said bend, said lead body foldable at said bend such that said first segment lies alongside and against said second segment;

sensor means for providing an output which varies as a function of said parameter, located distal to said bend on said first segment; and means for measuring the output of said sensor.

6. A cardiac pacemaker having a rate which varies as a function of a blood parameter, comprising:
   a pulse generator means for generating pacing pulses,
   a transvenous lead having proximal end and a distal end and having a "V" shaped bend near its distal end and having a first straight segment extending from said bend to said distal end and a second straight segment extending proximal from said bend, said lead body foldable at said bend such that said first segment lies alongside and against said second segment;
   sensor means for providing an output which varies as a function of said parameter located distal to said bend on said first segment; and
   means for varying the rate of said pacing pulses as a function of said output.

7. An implantable anti-tachycardia device having therapy which is delivered as a function of a blood parameter, comprising:
   means for delivering an antitachycardia therapy;
   a transvenous lead having proximal end and a distal end and having a "V" shaped bend near its distal end and having a first straight segment extending from said bend to said distal end and a second straight segment extending proximal from said bend, said lead body foldable at said bend such that said first segment lies alongside and against said second segment;
   sensor means for providing an output which varies as a function of a blood parameter, located distal to said bend on said first segment; and
   means for controlling the delivery of said therapy as a function of said output.

8. A method of measuring a blood parameter in a first blood vessel, comprising:
   positioning a sensor which provides an output which varies as a function of said blood parameter on a transvenous lead having a lead body having a formed bend near its distal end, such that said sensor is located distal to said bend;
   folding said lead at said bend such that said distal end is folded back against said lead body and advancing said folded lead through a second blood vessel which intersects said first blood vessel, until said distal end reaches said first blood vessel;
   withdrawing said lead to position said sensor in said first blood vessel; and
   employing said sensor to measures said blood parameter.

9. A method for regulating a pacing rate of a cardiac pacemaker as a function of a blood parameter, comprising:
   positioning a sensor which provides an output which varies as a function of said parameter on a transvenous lead having a lead body having a formed bend near its distal end, such that said sensor is located distal to said bend;
   folding said lead at said bend such that said distal end is folded back against said lead body and advancing said folded lead through a first blood vessel which intersects a second blood vessel, until the distal end of said lead reaches said second blood vessel;
   withdrawing said lead to position said sensor in said second blood vessel;
   employing said sensor within said second vessel to measure said parameter; and
   varying the pacing rate of said cardiac pacemaker as a function of said measured parameter.

10. A method of controlling a therapy delivered by an implantable anti-tachycardia device as a function of a blood parameter, comprising:
   positioning a sensor which provides an output which varies as a function of said parameter on a transvenous lead having a lead body having a formed bend near its distal end, such that said sensor is located distal to said bend;
   folding said lead at said bend such that said distal end is folded back against said lead body and advancing said folded lead through a first blood vessel which intersects a second blood vessel, until the distal end of said lead reaches said second blood vessel,
   withdrawing said lead to position said sensor to said second blood vessel;
   employing said sensor within said second blood vessel to measure said parameter; and
   controlling a therapy to be delivered as a function of said measured parameter.

* * * * *